United States Patent
Ogihara et al.

(10) Patent No.: US 8,740,797 B2
(45) Date of Patent: Jun. 3, 2014

(54) ULTRASONIC THERAPEUTIC APPARATUS

(75) Inventors: Makoto Ogihara, Chiba (JP); Jun Kubota, Chiba (JP); Akira Sasaki, Chiba (JP); Hiroshi Furuhata, Tokyo (JP); Toshihiro Ishibashi, Tokyo (JP)

(73) Assignee: The Jikei University, Tokyo (JP)

( * ) Notice: Subject to any disclaimer, the term of this patent is extended or adjusted under 35 U.S.C. 154(b) by 1550 days.

(21) Appl. No.: 11/993,047

(22) PCT Filed: Jun. 22, 2006

(86) PCT No.: PCT/JP2006/312513
§ 371 (c)(1),
(2), (4) Date: Dec. 19, 2007

(87) PCT Pub. No.: WO2006/137484
PCT Pub. Date: Dec. 28, 2006

(65) Prior Publication Data
US 2010/0222676 A1 Sep. 2, 2010

(30) Foreign Application Priority Data

Jun. 22, 2005 (JP) ................................. 2005-182334

(51) Int. Cl.
*A61B 8/00* (2006.01)
*A61B 8/12* (2006.01)
*A61N 7/02* (2006.01)

(52) U.S. Cl.
CPC .... *A61B 8/12* (2013.01); *A61N 7/02* (2013.01)
USPC ....................................................... 600/439

(58) Field of Classification Search
USPC ....................................................... 600/439
See application file for complete search history.

(56) References Cited

U.S. PATENT DOCUMENTS

| 3,569,924 A | * | 3/1971 | Drake et al. | 367/93 |
| 4,620,546 A | | 11/1986 | Aida et al. | |
| 5,744,457 A | * | 4/1998 | Weitz et al. | 514/56 |
| 5,984,881 A | * | 11/1999 | Ishibashi et al. | 601/2 |

(Continued)

FOREIGN PATENT DOCUMENTS

| JP | 61-013954 | 1/1986 |
| JP | 10-192289 | 7/1998 |

(Continued)

*Primary Examiner* — Tse Chen
*Assistant Examiner* — Hien Nguyen
(74) *Attorney, Agent, or Firm* — Antonelli, Terry, Stout & Kraus, LLP.

(57) ABSTRACT

An ultrasonic therapeutic apparatus according to the present invention being provided with: an ultrasonic probe (102) provided with a group of ultrasonic transducers for diagnosis use and a group of ultrasonic transducers for therapeutic use of which at least apart of ultrasonic beam irradiation surfaces are arranged so as to overlap each other, a tomographic image producing means (8) that produces a tomographic image containing a diseased portion of a subject from reflection echoes received by the group of ultrasonic transducers for diagnosis use, a display means (10) that displays the tomographic image containing the diseased portion of the subject produced by the tomographic image producing means (8), a setting means (103) that sets an irradiation path of the therapeutic ultrasonic waves on the tomographic image containing the diseased portion of the subject displayed by the display means (10) and a control means (104) that produces irradiation path information corresponding to the irradiation path of the therapeutic ultrasonic waves set by the setting means (103) and causes to display the produced irradiation path information on the display means (10) while correlating with the tomographic image containing the diseased portion of the subject.

7 Claims, 7 Drawing Sheets

(56) References Cited

U.S. PATENT DOCUMENTS

| | | |
|---|---|---|
| 6,451,009 B1* | 9/2002 | Dasilva et al. .................. 606/12 |
| 2002/0065507 A1* | 5/2002 | Zadno-Azizi ................ 604/509 |
| 2002/0067376 A1* | 6/2002 | Martin et al. ................. 345/810 |
| 2004/0073121 A1* | 4/2004 | Sun ............................... 600/485 |
| 2005/0124881 A1* | 6/2005 | Kanai et al. ................... 600/437 |

FOREIGN PATENT DOCUMENTS

| | | | |
|---|---|---|---|
| JP | 2000-210300 | * | 2/2000 |
| JP | 2000-210300 | | 8/2000 |
| JP | 2005-182334 | | 7/2005 |
| WO | WO 2004/066856 A1 | | 8/2004 |

* cited by examiner

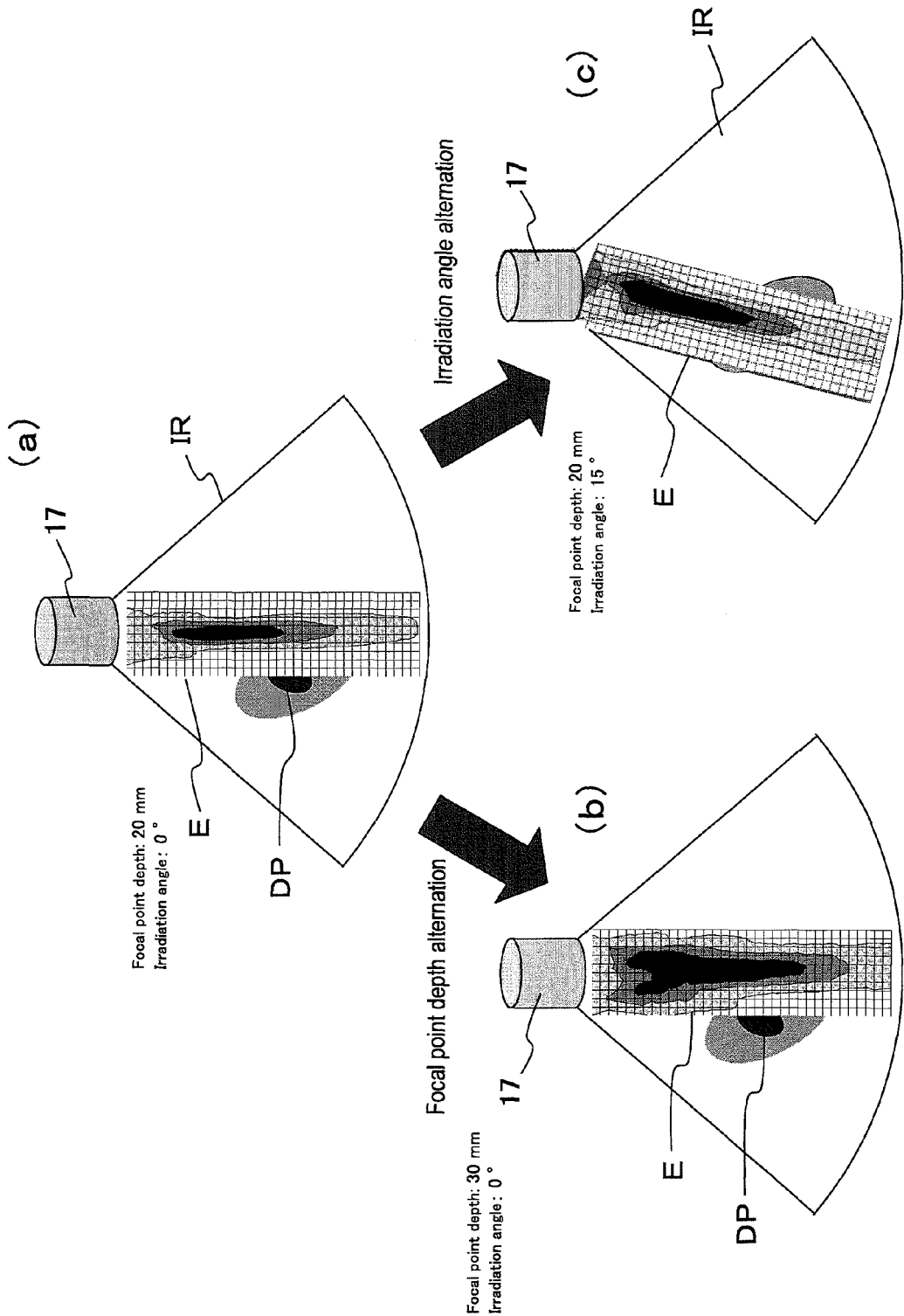

US 8,740,797 B2

ULTRASONIC THERAPEUTIC APPARATUS

FIELD OF THE INVENTION

The present invention relates to an ultrasonic therapeutic apparatus in which while displaying on a monitor an ultrasonic tomographic image containing a diseased portion including an embolized portion in a blood vessel or a tumor of a subject and by irradiating therapeutic ultrasonic waves of a proper intensity to the diseased portion to resolve the thrombus or to cauterize the tumor the diseased portion is treated.

The present application is an application claiming Paris Convention priority based on Japanese Patent Application No. 2005-182334 under Japanese Patent Law and is an application, which enjoys the benefit of Japanese Patent Application No. 2005-182334 by reference.

CONVENTIONAL ART

In a conventional ultrasonic therapeutic apparatus, at first diagnostic ultrasonic waves are irradiated toward a region including a diseased portion to be treated from ultrasonic transducers for diagnostic use and an ultrasonic tomographic image for diagnostic use from the reflected echo signals including the diseased portion is displayed on a monitor. An operator observes such as position, size, shape and surrounding living body tissue of the diseased portion to be treated in the ultrasonic tomographic image for diagnostic use including the diseased portion displayed on the monitor. The operator inputs from an input unit such as irradiation path including irradiation angle, focusing depth and irradiation intensity of therapeutic ultrasonic waves to be irradiated and sets the intensity of the therapeutic ultrasonic waves irradiated at a treatment position (irradiation position) and the irradiation position. Thereafter, the ultrasonic transducers for therapeutic use are controlled according to the irradiation position set by the operator so as to irradiate therapeutic ultrasonic waves toward the diseased portion.

A conventional therapeutic ultrasonic apparatus is disclosed in patent document 1. An operator designates on an ultrasonic tomographic image for diagnostic use displayed on a monitor an irradiation position where therapeutic ultrasonic waves are irradiated by making use of an input unit. The operator further inputs by making use of the input unit input conditions such as an output waveform, output value and output interval of the therapeutic ultrasonic waves. A control unit causes to display on the monitor a target cursor corresponding to the irradiation position of the therapeutic ultrasonic waves in a superposed manner on the ultrasonic image for diagnostic use according to the respective input data. The target cursor represents an irradiation intensity of output beams of the therapeutic ultrasonic waves by means of shape, size or color thereof.

Patent Document 1: JP-A-10-192289

However, in the above referred to conventional ultrasonic therapeutic apparatus, since information on the irradiation path such as irradiation intensity distribution along the irradiation path of the therapeutic ultrasonic waves is insufficient, no consideration for observing influences on normal portions in the irradiation path of the therapeutic ultrasonic waves is given.

An object of the present invention is to provide an ultrasonic therapeutic apparatus that is able to observe influences on normal portions in the irradiation path of the therapeutic ultrasonic waves.

SUMMARY OF THE INVENTION

An ultrasonic therapeutic apparatus according to the present invention is characterized by comprising an ultrasonic probe (102) provided with a group of ultrasonic transducers for diagnosis use and a group of ultrasonic transducers for therapeutic use of which at least a part of ultrasonic beam irradiation surfaces are arranged so as to overlap each other, a tomographic image producing means (8) that produces a tomographic image containing a diseased portion of a subject from reflection echoes received by the group of ultrasonic transducers for diagnosis use, a display means (10) that displays the tomographic image containing the diseased portion of the subject produced by the tomographic image producing means (8), a setting means (103) that sets an irradiation path of the therapeutic ultrasonic waves on the tomographic image containing the diseased portion of the subject displayed by the display means (10) and a control means (104) that produces irradiation path information corresponding to the irradiation path of the therapeutic ultrasonic waves set by the setting means (103) and causes to display the produced irradiation path information on the display means (10) while correlating with the tomographic image containing the diseased portion of the subject.

According to the present invention, influences on normal portions in the irradiation path of the therapeutic ultrasonic waves can be observed.

BRIEF DESCRIPTION OF THE DRAWINGS

FIG. 7 is views showing alternative examples of focusing depth or irradiation angle from FIG. 6.

BEST MODE FOR CARRYING OUT THE INVENTION

Figure 1:
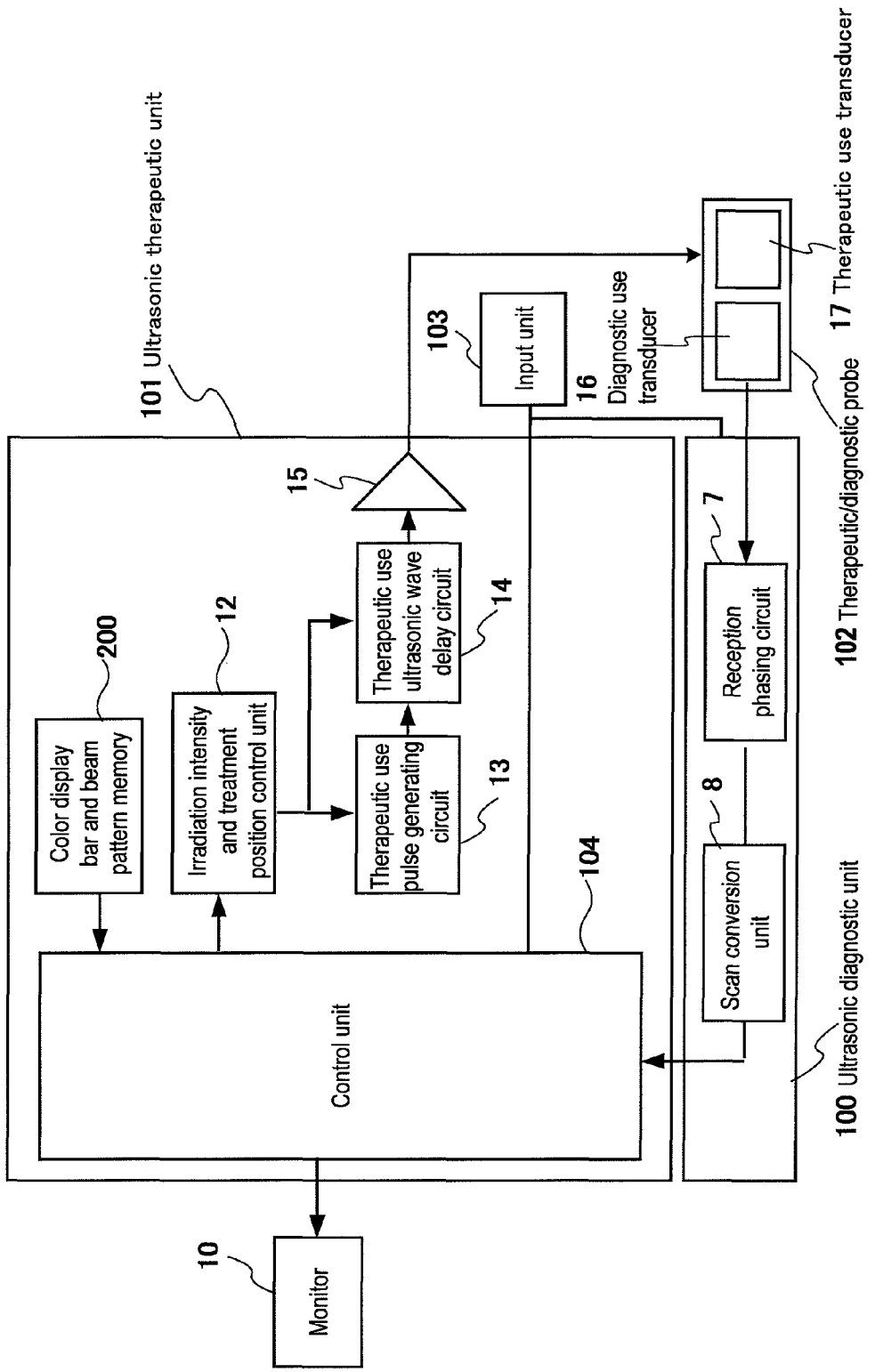
FIG. 1 is a schematic block diagram of an ultrasonic therapeutic apparatus representing an embodiment of the present invention.
Figure 2:
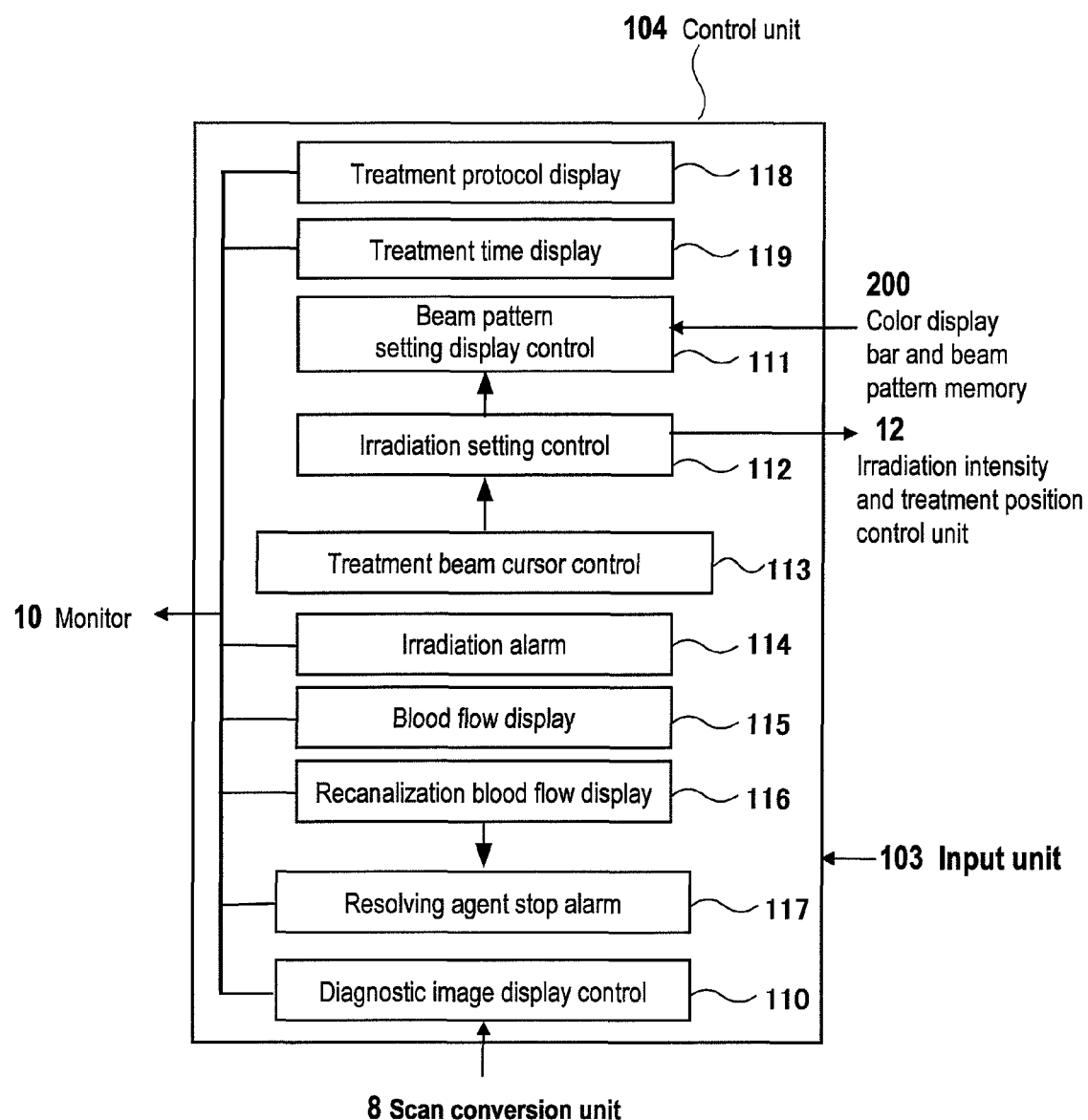
FIG. 2 is a functional block diagram of one constitutional example of a control unit 104 in FIG. 1.
Figure 3:
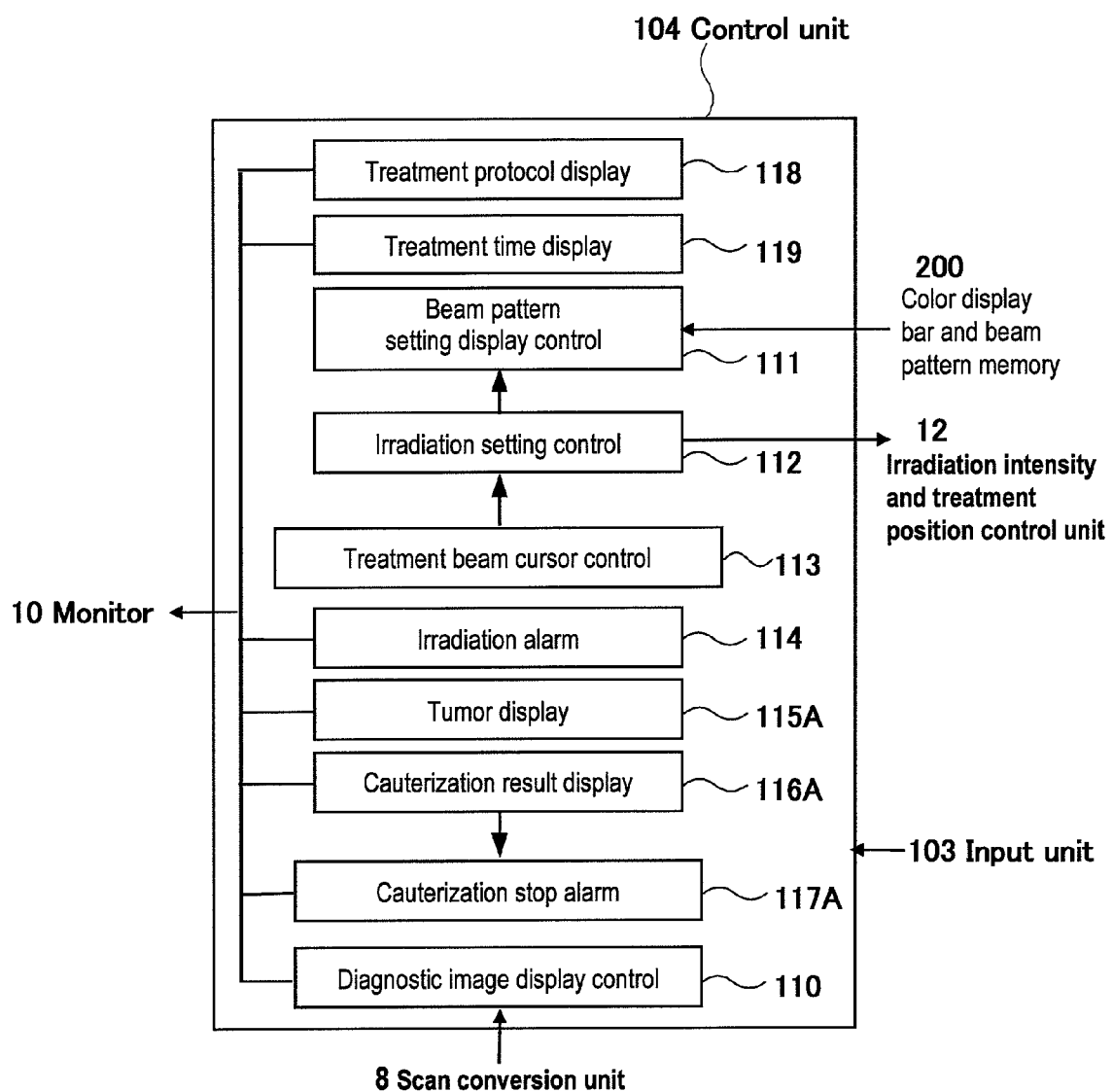
FIG. 3 is a functional block diagram of another constitutional example from FIG. 2.

An embodiment of an ultrasonic therapeutic apparatus according to the present invention will be explained with reference to FIG. 1 through FIG. 4.

The ultrasonic therapeutic apparatus according to the present embodiment includes the following constitutional elements.

The ultrasonic diagnostic unit 100 transmits ultrasonic waves to a portion containing a diseased portion of a subject, produces a B mode image (tomographic image) containing the diseased portion from the reflected echo signals by a scan conversion unit 8 and displays the produced tomographic image on a monitor 10. Herein, since the ultrasonic diagnostic unit 100 is a prior art ultrasonic diagnostic device, the detailed explanation thereof is omitted.

An ultrasonic therapeutic unit 101 includes the following constitutional elements that are connected to the ultrasonic diagnostic unit 100 so as to permit data transmission therewith. A therapeutic use pulse generating circuit 13 drives therapeutic use transducers 17 and irradiates therapeutic use ultrasonic waves toward a treatment position of a set diseased portion of a subject. A therapeutic use ultrasonic wave delaying circuit 14 properly delays the therapeutic ultrasonic waves and forms a focusing point of the therapeutic ultrasonic waves. An amplifier 15 signal-amplifies the therapeutic ultrasonic waves. An irradiation intensity and therapeutic position control unit 12 controls the therapeutic use pulse generating circuit 13 and the therapeutic use ultrasonic wave delaying circuit 14. A control unit 104 controls the irradiation intensity and therapeutic position control unit 12 and the monitor 10.

The monitor 10 is connected to the ultrasonic therapeutic unit 101 so as to permit data transmission therewith and includes a therapeutic/diagnostic probe 102 that is connected to the ultrasonic diagnostic unit 100 and the ultrasonic therapeutic unit 101 so as to permit transmission and reception of the ultrasonic wave signals therewith and an input unit 103 that is connected to the therapeutic/diagnostic probe 102, the ultrasonic diagnostic unit 100 and the ultrasonic therapeutic unit 101 so as to permit transmission and reception of control signals thereto.

The input unit 103 is constituted so as to permit inputting of such as a variety of commands and set values.

The therapeutic/diagnostic probe 102 is constituted by diagnostic use transducers 16 and therapeutic use transducers 17 and the both are constituted integrally, for example, through lamination so that their beam irradiation planes occupy a same plane. The therapeutic/diagnostic probe 102 is held on a body surface near the diseased portion of the subject with a hand of an operator or by making use of a holding tool.

The ultrasonic diagnostic unit 100 drives the diagnostic use transducers 16 through a diagnostic use pulse generating circuit, a diagnostic use ultrasonic wave delaying circuit and an amplifier.

Figure 4:
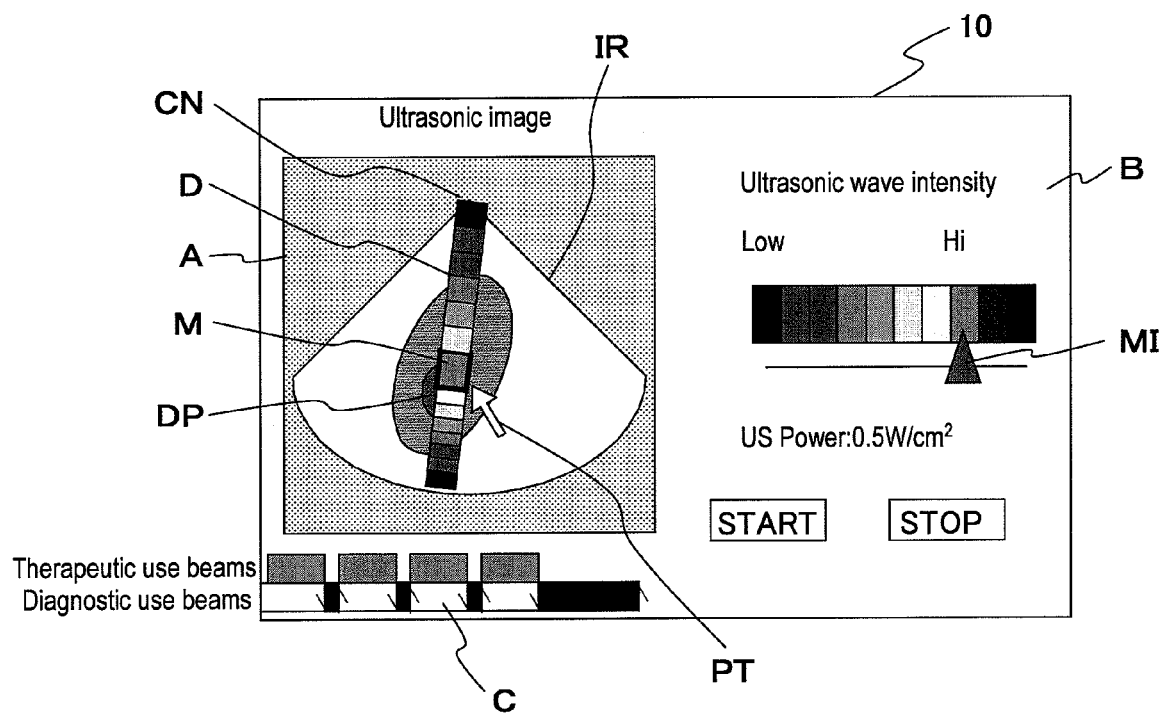
FIG. 4 is a view showing a display example on a monitor 10 by the control unit 104 in FIG. 1.

The diagnostic use transducers 16 thus driven irradiate diagnostic use ultrasonic waves toward a region containing the diseased portion of the subject, receive the reflected waves, convert the same into electrical signals and transfer the same to a received wave phasing circuit 7. Signals subjected to a phasing process herein are inputted through the scan conversion unit 8 to a diagnostic image display control unit 110 included in the control unit 104 of the ultrasonic therapeutic unit 101 and in the diagnostic image display control unit 110 the imaging process is performed and a diagnostic use ultrasonic image A as shown in FIG. 4 is displayed on the monitor 10.

The ultrasonic wave therapeutic unit 101 includes the following constitutional elements. The therapeutic use pulse generating circuit 13 drives therapeutic use transducers 17 and causes to irradiate therapeutic use ultrasonic waves toward the treatment position of the set diseased portion of the subject. The irradiation intensity and therapeutic position control unit 12 controls the therapeutic use ultrasonic wave delaying circuit 14, the amplifier 15, the therapeutic use pulse generating circuit 13 and the therapeutic use ultrasonic wave delaying circuit 14. The control unit 104 controls the irradiation intensity and therapeutic position control unit 12 and the monitor 10. The control unit 104 further includes a beam pattern setting display control unit 111 and a beam pattern memory 200. The beam pattern memory 200 stores color display bars of plural kinds to which data of a desired color display bar is accessible from the beam pattern setting display control unit 111.

In addition to the diagnostic image display control unit 110 and the beam pattern setting display control unit 111, and a therapeutic protocol display unit 118 and a therapeutic period display unit 119, the control unit 104 includes constitutional elements for at least one function for thrombus resolving and for tumor cauterizing. The constitutional elements for the thrombus resolving function include an irradiation setting control unit 112, a therapeutic beam cursor control unit 113, an irradiation alarming unit 114, a blood flow display unit 115 and a resolving agent stop alarming unit 117. Further, the constitutional elements for the tumor cauterizing function include a tumor display unit 115A, a recanalized blood flow display unit 116 or a cauterized result display unit 116A and a cauterizing stop alarming unit 117A.

Prior to starting a treatment by directing the therapeutic use transducers 17 in the ultrasonic therapeutic unit 101 toward a treatment position of a diseased portion set in a subject and irradiating therapeutic use ultrasonic waves, a treatment planning according to the present embodiment is performed in the following manner.

At first, while observing the diagnostic use ultrasonic image A displayed on the left half region on the monitor 10, the operator moves the therapeutic beam cursor in the input unit 103 to the center portion of a diseased portion DP to be treated and sets the treatment position. For example, by making use of a mouse pointer PT in the input portion 103 the therapeutic beam cursor control unit 113 is controlled. The coordinate of the set treatment position is transferred to the irradiation setting control unit 112 from the therapeutic beam cursor control unit 113. Thereafter, herein the focusing depth and the irradiation angle of the therapeutic use ultrasonic waves to be irradiated are computed based on the transferred coordinate of the treatment position.

Further, the operator, while observing the set treatment position on the monitor 10, inputs an. intensity of the therapeutic use ultrasonic waves to be irradiated to the set treatment position by making use of, for example, a key board in the input unit 103. The inputted intensity of the therapeutic use ultrasonic waves is likely transferred to the irradiation setting control unit 112.

The focusing depth and the irradiation angle computed in the irradiation setting control unit 112 and the inputted intensity of the therapeutic use ultrasonic waves are transferred to the beam pattern setting display control unit 111.

The beam pattern setting display control unit 111 is connected to the color display bar and beam pattern memory 200 in a manner to be accessible thereto. Further, at the right side on the monitor 10 as shown in FIG. 4 a moving indicator MI is displayed. The intensity of ultrasonic waves at a position where the moving indicator is placed is, for example, 0.5 W/cm$^2$ and a reference use ultrasonic wave intensity color display bar B is displayed by color-coding in 10 levels with a unit of 0.05 W/cm$^2$. In the beam pattern memory 200, data for displaying the reference use ultrasonic wave intensity color display bar B and data for position information and strip shaped beam patterns are stored. The position information uses parameters of angle and depth from a position CN of the ultrasonic transducers 17 in an ultrasonic imaging range IR. The ultrasonic intensity distribution corresponds to the entire region of the color-coded sections of the reference use ultrasonic wave intensity color display bar B. The data are those obtained along the irradiation path of the therapeutic use ultrasonic waves, for example, with regard to 64×16=1024 data points.

The beam pattern data representing the ultrasonic wave intensity distribution with regard to the respective data points are measured before shipment by making use of, for example, a hydrophone and are stored in the memory 200 after patterning in a form such as a bit map image.

The color display of the reference use ultrasonic wave intensity color display bar B is color-coded and sectioned from the left end having low ultrasonic wave intensity to the right end having high ultrasonic wave intensity, for example, in such a manner that while determining the left end as blue, the blue torn gradually decreases and red torn gradually increases.

The beam pattern setting display control unit 111 captures from the color display bar and beam pattern memory 200 a beam pattern of the data point corresponding to the irradiation angle and the focusing depth inputted from the irradiation setting control unit 112. The captured beam pattern represents a sectioned ultrasonic wave distribution. The beam pattern setting display control unit 111 performs coloring according to the irradiation intensity of the inputted treatment position, namely the focused position in correspondence with the color sections of the reference use ultrasonic wave intensity color display bar B. The coloring is performed on the displayed diagnostic use ultrasonic wave image A along the therapeutic use ultrasonic wave irradiation path or along a running direction of a hollow organ of the diseased portion. A strip shaped therapeutic use ultrasonic beam pattern D colored in such a manner is displayed by being superposed on the diagnostic use ultrasonic wave image. In this instance, in order to ease observation of the organ and the diseased portion on the therapeutic use ultrasonic wave irradiation path, the strip shaped therapeutic use ultrasonic beam pattern D can be displayed in a superposed manner on the diagnostic use ultrasonic wave image after being processed in semi-transparent.

The operator observes the strip shaped therapeutic use ultrasonic beam pattern D displayed while being superposed on the diagnostic use ultrasonic wave image A. The operator confirms the followings through this observation. (1) Whether the ultrasonic wave intensity and its spreading of the section represented by M among the beam pattern D irradiated to the diseased portion DP are proper. (2) Whether there exists such as an organ that is weak to ultrasonic waves on the ultrasonic wave irradiation path. When it is judged there are no problems with regard to these items to be confirmed, the operator pushes a START button through the input unit 103 or on the monitor 10. The ultrasonic therapeutic unit 101 drives the irradiation intensity and therapeutic position control unit 12, the therapeutic use pulse generating circuit 13, the therapeutic ultrasonic wave delaying circuit 14, the amplifier 15 and the therapeutic use transducers 17 according to the set value including the beam pattern D, and starts irradiation of the therapeutic use ultrasonic waves toward the diseased portion D.

Further, in order to have the operator correctly grasp the ultrasonic wave intensity of the section M corresponding to the treatment position in the therapeutic use ultrasonic beam pattern D, the region of the corresponding color section on the reference use ultrasonic wave intensity color display bar B can be displayed in flickering manner.

When the operator judges the ultrasonic wave intensity distribution including irradiation intensity on the diseased portion DP is improper, the operator resets the ultrasonic wave intensity to be irradiated and the irradiation position through the input unit 103. The resetting of the irradiation position can be performed by a measure in which, for example, the moving indicator MI on the reference use ultrasonic wave intensity color display bar B is moved to shift the position of reference ultrasonic wave intensity on the color display bar. Further, when the moving indicator MI is moved, the band of the ultrasonic wave intensity covered by the color display bar B also varies.

Further, when there is a portion to which irradiation of ultrasonic waves should be avoided on the ultrasonic wave irradiation path, the position of the therapeutic/diagnostic probe 102 on the body surface is altered and the treatment position and the irradiation intensity are reset.

The strip shaped therapeutic use ultrasonic beam pattern D displayed in a superposed manner on the diagnostic use ultrasonic wave image A represents colored intensity distribution corresponding to the color sections of the reference use ultrasonic wave intensity color display bar B. Therefore, the operator can visibly and instantly recognize the distribution of the therapeutic use ultrasonic wave intensity to be irradiated, thereby, can easily judge the properness.

At the same time, in the stage of treatment planning according to the present embodiment before starting the treatment by irradiating the therapeutic use ultrasonic wave, the operator inputs the treatment protocol data in the treatment protocol display unit 118 in the control unit 104 through the input unit 103. A display C on the monitor 10 in FIG. 4 is an example of a displayed treatment protocol and shows timing and sequence of irradiation of the therapeutic use ultrasonic beams during treatment and of the diagnostic use ultrasonic beams (irradiation resting of the therapeutic use ultrasonic beams).

The treatment period display unit 119 in the control unit 104 displays on the monitor 10 the lapsed time from the start of the treatment in a numerical value or in an arrow in a manner being superposed on the displayed treatment protocol C or in parallel therewith.

The irradiation alarming unit 114 audibly or optically alarms that thrombus resolution accelerating ultrasonic beams are in a way of being irradiated during the therapeutic use ultrasonic wave irradiation.

The blood flow display unit 115 monitors blood flow in a blood vessel portion at an embolized peripheral region that is set as a treatment position during the treatment planning stage and displays on the monitor 10 a velocity or flow rate or both of the recanalized blood flow in numerical values.

The tumor display unit 115A monitors the degree of cauterization of the tumor portion set as a treatment position during the treatment planning stage and displays the same on the monitor 10.

When the blood flow velocity or flow rate thereof measured at the time of blood flow recanalization due to thrombus resolution exceeds predetermined values, the recanalizing blood flaw display unit 116 indicates and displays the fact audibly or optically or in both.

When the degree of cauterization of the tumor portion exceeds a predetermined level, the cauterization result display unit 116A indicates and displays the fact audibly or optically or in both.

When the blood flow recanalization reaches a set blood flow condition (Flow velocity or flow rate or both) and thereafter a predetermined time elapses, the resolving agent stop alarming unit 117 alarms audibly or optically or in both for commanding to stop supplying the thrombus resolving agent.

When the degree of cauterization of the tumor portion reaches a predetermined level, the cauterization stop alarming unit 117A alarms audibly or optically or in both for commanding to stop the cauterization.

A series of operational flow from the treatment planning to the irradiation of the therapeutic use ultrasonic beams will be summarized and explained with reference to FIG. 5 flowchart which is performed by the embodiment of the ultrasonic therapeutic apparatus according to the present invention as explained hitherto with reference to FIG. 1 through FIG. 4.

At first, in step ST1, the diagnostic use ultrasonic wave image A, which is obtained through signal processing the reflected waves from the diseased portion of the irradiated diagnostic ultrasonic waves and received by the diagnostic use transducers 16, is displayed on the monitor 10.

In step ST2, after observing the diagnostic use ultrasonic wave image A displayed on the monitor 10, the operator inputs an initial value of intensity of the therapeutic use ultrasonic waves to be irradiated to the diseased portion DP of the subject through the input unit 103.

In step ST3, while observing the diagnostic use ultrasonic wave image A displayed on the monitor 10, the operator moves by making use of, for example, the mouse pointer PT in the output unit 103 the therapeutic beam cursor controlled by the therapeutic beam cursor control unit 113 to the center portion of the diseased portion to be treated to set the treatment position. Further, the order of the steps ST2 and ST3 can be altered.

In step ST4, the therapeutic beam cursor control unit 113 reads the coordinate of the set therapeutic position and inputs the same to the irradiation setting control unit 112.

In step ST5, the irradiation setting control unit 112 calculates the angle and the depth of the data point, namely, the focal point of the therapeutic use ultrasonic waves to be irradiated based on the inputted coordinate of the treatment position. The irradiation setting control unit 112 further inputs the calculated angle and depth of the focal point into the beam pattern setting display control unit 111 together with the previously inputted data of the therapeutic use ultrasonic wave intensity.

In step ST6, the beam pattern setting display control unit 111 calls a beam pattern including a distribution pattern of the ultrasonic wave intensity at the data point corresponding to the inputted angle and depth of the focal point from the color display bar and beam pattern memory 200. Further, the beam pattern setting display control unit 111 produces on the displayed color display bar the strip shaped therapeutic use ultrasonic beam pattern D by applying corresponding colors allocated to the respective ultrasonic wave intensity with reference to the ultrasonic wave intensity at the inputted focal point. The respective intensity sections of the strip shaped therapeutic use ultrasonic beam pattern D accompanies the distribution of the called ultrasonic wave intensity. The strip shaped therapeutic use ultrasonic beam pattern D is displayed on the diagnostic use ultrasonic wave image A displayed on the monitor 10 in a superposed manner along the irradiation path of the therapeutic use ultrasonic waves.

In step ST7, the beam pattern setting display control unit 111 references the displayed color in the reference use ultrasonic wave intensity color display bar B displayed in parallel on the monitor 10. With reference to the displayed color in the reference use ultrasonic wave intensity color display bar B, the operator sets the strip shaped therapeutic use ultrasonic beam pattern D accompanying the colored ultrasonic wave distribution information displayed in a superposed manner on the diagnosis use ultrasonic wave image A on the monitor 10. Thereby, display information is provided for the operator to judge whether the distribution of the ultrasonic intensity along the irradiation path containing the treatment position and whether the irradiation path thereof are proper.

Figure 5:
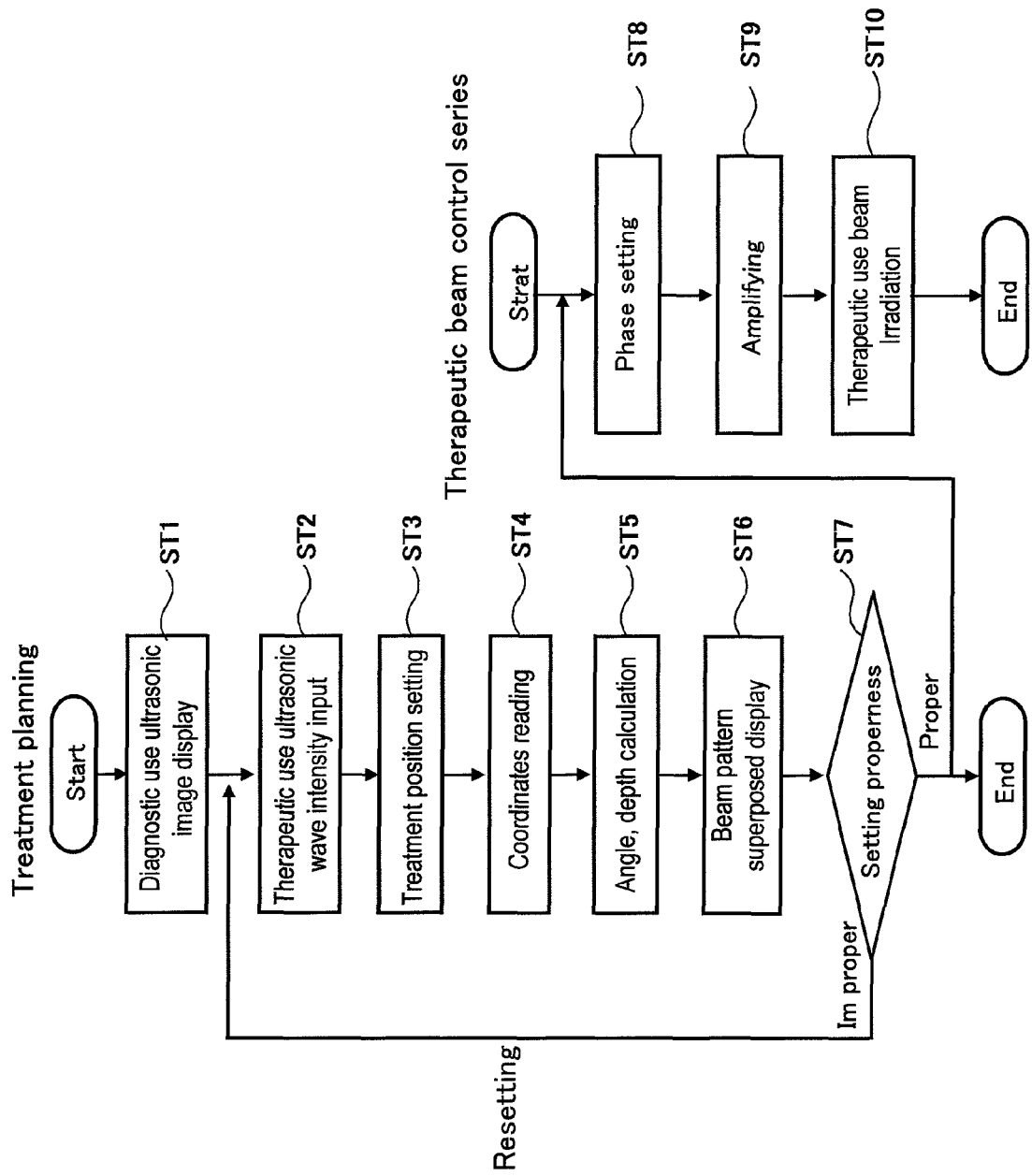
FIG. 5 is a flowchart showing an operation example of the ultrasonic therapeutic apparatus in FIG. 1.

When the setting is judged proper in step ST7, the process moves to the therapeutic use beam control system at the right side in FIG. 5 and in step ST8, the therapeutic use ultrasonic wave delay circuit 14 drives the respective therapeutic use transducers 17 based on the angle and the depth of the set focal point such as in the strip shaped therapeutic use ultrasonic beam pattern D. The phases of the drive signals for these therapeutic use transducers 17 are set therewith. In step ST9, the drive signals are amplified. In step ST10, the respective therapeutic use transducers 17 are driven based on the amplified drive signals and the irradiation of the therapeutic use ultrasonic waves toward the diseased portion of the subject is started.

When the setting is judged improper in step ST7, the process returns to step ST2 wherein the intensity of the therapeutic use ultrasonic waves is reset and in step ST3, the treatment position is reset. Further, the irradiation path of the therapeutic use ultrasonic waves is judged improper, the process returns to step ST1 and the position of the therapeutic/diagnostic probe 102 on the body surface is altered and a new diagnostic use ultrasonic wave image A is displayed on the monitor 10, thereafter, step ST2~step ST7 are executed again.

Figure 6:
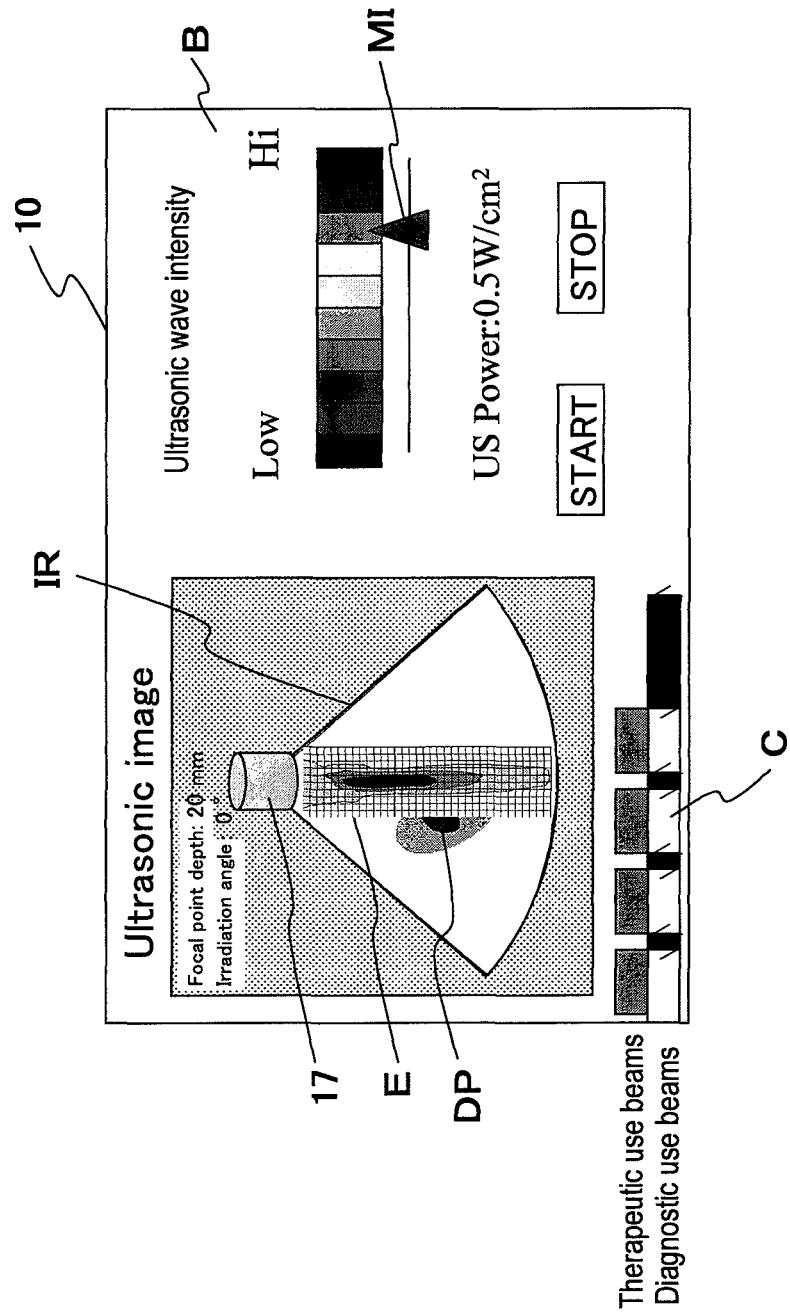
FIG. 6 is another display example from FIG. 4.

FIG. 6 shows a display example on the monitor 10 wherein a second type beam pattern E is used for the ultrasonic therapeutic apparatus according to the present invention in place of the first type of the strip shaped beam pattern D as shown in FIG. 4.

The second type of the beam pattern includes information of ultrasonic wave intensity distribution in lateral direction perpendicular to the direction along the irradiation path of the therapeutic use ultrasonic waves in addition to the information of ultrasonic wave intensity distribution in the direction along the irradiation path.

Accordingly, when the second type of the beam pattern E is displayed in a superposed manner on the diagnostic ultrasonic wave image displayed on the monitor 10, the distribution of therapeutic use ultrasonic wave intensity in a comparatively broad area around the diseased portion of the subject can be observed. Thereby, the properness of the set irradiation condition can be judged further correctly.

In the same manner as for the first type of the beam pattern D, the beam pattern data representing the ultrasonic wave intensity distribution with regard to the respective data points in the second type beam pattern E are also measured before shipment by making use of, for example, a hydrophone and are stored in the memory 200 after patterning in a form such as a bit map image.

FIG. 7(*a*) shows a display example of the second type beam pattern E corresponding to a treatment position at focusing point depth of 20 mm and irradiation angle of 0° displayed in a superposed manner on the diagnosis use image in the ultrasonic wave imaging range IR on the monitor 10. FIG. 7(*b*) shows a display example of the second type beam pattern E corresponding to a treatment position at focusing point depth of 30 mm and irradiation angle of 0° displayed in a superposed manner on the diagnosis use image in the ultrasonic wave imaging range IR on the monitor 10. FIG. 7(*c*) shows a display example of the second type beam pattern E corresponding to a treatment position at focusing point depth of 20 mm and irradiation angle of 15° displayed in a superposed manner on the diagnosis use image in the ultrasonic wave imaging range IR on the monitor 10.

In the like manner as explained in connection with FIG. 1~FIG. 5, while observing the colored ultrasonic wave intensity distribution including a spread also in lateral direction in the second type beam pattern E displayed in a superposed manner on the respective diagnostic use images, the operator judges the properness of the previous setting.

According to the present embodiment, prior to the treatment of the diseased portion of the subject by the irradiation of therapeutic use ultrasonic waves, the treatment position and the irradiation intensity of the therapeutic use ultrasonic waves can be set by making use of the diagnostic use ultrasonic wave tomographic image displayed on the monitor. Further, since confirmation and evaluation of the setting properness of the irradiation intensity is easy, the ultrasonic therapy can be performed smoothly.

The invention claimed is:
1. An ultrasonic therapeutic apparatus comprising:
 an ultrasonic probe provided with therapeutic use transducers and diagnostic use transducers having a common ultrasonic beam irradiation surface;

a monitor that displays a diagnostic use tomographic image containing a diseased portion of a subject that is produced by processing reflection echoes received by the diagnostic use transducers; and an input unit through which a position of therapy in the diseased portion of the subject is input on the diagnostic use tomographic image containing a diseased portion of the subject displayed on the monitor as well as input an intensity of the therapeutic use ultrasonic beam to be irradiated at the position of therapy;

characterized by further comprising:

a color display bar and beam pattern memory configured to store both beam pattern data including ultrasonic beam intensity distribution patterns at respective points in a region covered by the diagnostic use tomographic image according to parameters including irradiation angle of therapeutic use ultrasonic beam seen from a setting position of the ultrasonic probe on a body surface of the subject and a focus depth thereof that are determined in advance, and therapeutic use ultrasonic beam intensity data sectioned in plural levels by a predetermined ultrasonic beam intensity unit and color data allotted to the respective leveled sections for a therapeutic use reference ultrasonic beam intensity color display bar to be displayed on the monitor in parallel with the diagnostic use tomographic image; and a beam pattern setting and display control unit configured to call a beam pattern including an ultrasonic beam intensity distribution pattern of a concerned point in the region covered by the diagnostic use tomographic image from the color display bar and beam pattern memory based on the position of therapy in the diseased portion of the subject and the intensity of the therapeutic use ultrasonic beam to be irradiated at the position of therapy that are input through the input unit, apply respective colors corresponding to the leveled ultrasonic beam intensity sections on the therapeutic use reference ultrasonic beam intensity color display bar displayed on the monitor to the ultrasonic beam intensity distribution pattern of the called beam pattern with reference to the input therapeutic use ultrasonic beam intensity to be irradiated at the diseased portion of the subject, and cause display of the color-coded ultrasonic beam intensity distribution pattern of the called beam pattern along the irradiation path of the therapeutic use ultrasonic beam and over the diagnostic use tomographic image displayed on the monitor in a superposed manner.

2. An ultrasonic therapeutic apparatus according to claim 1, wherein the beam pattern including ultrasonic beam intensity distribution patterns are strip shaped patterns.

3. An ultrasonic therapeutic apparatus according to claim 1, wherein the beam pattern including ultrasonic beam intensity distribution patterns further contain ultrasonic beam intensity information in lateral direction with respect to the irradiation path of the therapeutic use ultrasonic beam.

4. An ultrasonic therapeutic apparatus according to claim 1, wherein the beam pattern including ultrasonic beam intensity distribution patterns are semi-transparent.

5. An ultrasonic therapeutic apparatus according to claim 1, wherein a leveled ultrasonic beam intensity section on the therapeutic use reference ultrasonic beam intensity color display bar displayed on the monitor is designed to flicker that corresponds to the ultrasonic beam intensity of the section corresponding to the diseased portion of the subject in the beam pattern including an ultrasonic beam intensity distribution pattern displayed in a superposed manner over the diagnostic use tomographic image on the monitor.

6. An ultrasonic therapeutic apparatus according to claim 1, wherein the therapeutic use reference ultrasonic beam color display bar displayed on the monitor includes a moving indicator that indicates a reference position of ultrasonic beam intensity on the therapeutic use reference ultrasonic beam intensity color display bar, and the reference position of the ultrasonic beam intensity is altered by moving the moving indicator.

7. An ultrasonic therapeutic apparatus according to claim 1, further comprising an irradiation alarming unit that generates an audible or optical alarm or both when the therapeutic use transducers are irradiating the therapeutic use ultrasonic beam.

* * * * *